United States Patent [19] [11] 4,186,253
Yokoyama et al. [45] Jan. 29, 1980

[54] PERFUSATE FOR PRESERVING ORGAN TO BE TRANSPLANTED AND PRESERVING METHOD

[75] Inventors: Kazumasa Yokoyama, Toyonaka; Masakazu Iwai, Matsubara; Hiroyuki Okamoto, Akashi; Noboru Yamada, Amagasaki, all of Japan

[73] Assignee: The Green Cross Corporation, Osaka, Japan

[21] Appl. No.: 950,071

[22] Filed: Oct. 10, 1978

[51] Int. Cl.$^2$ ............... C12B 3/00; A61K 31/025
[52] U.S. Cl. ................................ 435/240; 424/352
[58] Field of Search ..................... 195/1.7; 424/352

[56] References Cited

U.S. PATENT DOCUMENTS

| | | | |
|---|---|---|---|
| 3,911,138 | 10/1975 | Clark | 424/352 |
| 3,962,439 | 6/1976 | Yokoyama | 424/352 |

*Primary Examiner*—Sam Rosen
*Attorney, Agent, or Firm*—Cushman, Darby & Cushman

[57] ABSTRACT

An organ to be transplanted, such as kidney, can effectively be preserved by perfusion for a considerably long time by the use of a perfusate which is made by mixing a Ringer's solution modified by increasing potassium ion to 8–20 meq/l, a stable perfluorocarbon compound emulsion and albumin, so that the concentration of the perfluorocarbon compound is 7.5 to 12.5% (W/V) and that of albumin is 1–8% (W/V) based on the perfusate.

16 Claims, No Drawings

PERFUSATE FOR PRESERVING ORGAN TO BE TRANSPLANTED AND PRESERVING METHOD

This invention relates to a perfusate for preserving an organ to be transplanted and preserving method by the use of the same and, more particularly, to a method for preserving an organ to be transplanted by using as perfusate a mixture comprising a modified Ringer's solution, used as basal salt solution, albumin and a perfluorocarbon emulsion.

In recent years, the technical progress in preserving an organ for transplantation is remarkable; especially the progress in the technique for preserving kidneys has ever promoted the propagation of cadaveric kidney transplantation. Such a progress is much indebted to the improvement of perfusate. For instance, the clinical methods for preserving kidneys for transplantation are broadly classified into two categories, the one being the hypothermic storage (by immersion) [Lancet, 2, 1219–1222 (1969)] and the other the hypothermic continuous perfusion [Lancet, 2, 536 (1967)]. In actual practice, the former is used in short period preservation and the latter in long period preservation. With further prepagation of cadaveric kidney transplantation, the long period preservation, that is, perfusional preservation will gain in importance.

In cadaveric kidney transplantation, since most of the kidneys are donated by the individuals who ran into accidents, the necessary steps to be taken between the time of emergence of a cadaveric kidney and the time of transplantation include histcompatibility testings between the cadaveric kidney and the patient, selection of a competent recipient, transportation of the donated kidney, and preparations for the transplantation. For these reasons, it is necessary to preserve the donated kidney as long as possible. In fact, as a part of studies on the cadaveric kidney transplantation, many attempts have heretofore been made to preserve the cadaveric kidney for a long period of time. One of the primary objects of these attempts is the development and improvement of perfusates.

The ever spreading clinical use of the hypothermic continuous perfusion originates from the research work of Belzer et al. [Lancet 536 (1967)]. They succeeded in preserving a canine kidney for 72 hours by employing as the perfusate a plasma freed from fibrinogen as far as possible prepared by freezing and melting a cryoprecipitated plasma. Since the publication of their report, chiefly the cryoprecipitated plasma has been employed as a perfusate for kidneys.

In 1974, Toledo-Pereyra et al. [Surg, Gynecol. Obstet, 138, 901–905 (1974)] developed a new perfusate of silica gel-treated cryoprecipitated plasma which is free from $\beta$-lipoprotein of fibrinogen still remained in the conventional cryoprecipitated plasma, and in which the level of insoluble fat fraction, i.e. triglycerids, has been reduced to one-third. The conventional cryoprecipitated plasma involved a great risk of emboli formation during the perfusion, which is caused by the residual fibrinogen, lipoprotein or neutral fat globules, whereas the risk is greatly reduced with the cryoprecipitated plasma treated with silica gel, which has been developed by Joledo-Pereyla et al. Such cryoprecipitated plasmas, however, still have several problems. Firstly, the preparative procedure has not been perfectly established and the composition of the prepared plasma tends to fluctuate, making it difficult to obtain preparations of constant protein content and constant electrolyte composition. Secondly, there exists still some fear of fat emboil formation during perfusion due to incomplete removal of the insoluble fat fraction. In order to reduce the risk, it is necessary to use an expensive membrane oxygenator. Thirdly, an important and essential problem is the lack of an adequate inactivation treatment against hepatitis virus, leading to the fear of possible infection with hepatitis virus. Although the cryoprecipitated plasma is an excellent perfusate for the preservation of kidney, yet it has several defects as mentioned above.

It was reported that in order to overcome the above difficulties associated with the cryoprecipitated plasma, an attempt was made to use an albumin solution as the perfusate and achieved a success in animal experiment. Grundman et al [Transpl., 17, 299–305 (1974)] perfused a canine kidney with a 6% albumin solution and successfully preserved the kidney for 96 hours. Their perfusate was a Krebs Ringer's solution containing 6% (W/V) of human albumin. The canine kidney perfused for 96 hours at a low temperature was autotransplanted and the graft survival was over 80%, indicating that the albumin solution is an excellent perfusate comparable favorably to the cryoprecipitated plasma.

The long-period preservation of a kidney requires a perfusate having a certain colloid osmotic pressure at low temperatures as well as an adequate electrolyte composition and, in addition, a certain amount of oxygen. When preserved at low temperatures, the kidney consumes much less oxygen than when at room temperature, yet requires a certain amount of oxygen in order to maintain its function. According to a classic study of Levy [American Journal Physiology 197, 1111–1114, (1959)], the oxygen consumption of a kidney at 8° to 10° C. is about 3 $\mu$l/g/minute which correspond to about 20% of the consumption at room temperature. Accordingly, in preserving a kidney it is a general practice to perfuse it with a perfusate while being oxygenated.

A saturated perfluoro organic compound (hereinafter referred to as PFC) is a liquid capable of dissolving a considerable volume of oxygen and functions as an oxygen carrier when used in the form of emulsion. Developmental researches are in progress on an artificial blood which utilizes the above-noted characteristic property of the PFC emulsion. The PFC emulsion well functions as an oxygen carrier either in vivo or in vitro (in an excorporeal system such as a perfusion system). Such a property suggests that a PFC emulsion can be utilized to advantage as an oxygen carrier in kidney preservation. Beside being a good solvent for oxygen, the selected PFC is biologically inert and presents no problem of direct toxicity to tissues. Therefore, when it is used as perfusate in preserving a kidney, no problems concerning toxicity will be aroused.

The studies on the preservation of a kidney by the use of a PFC emulsion started quite recently and originate from the work of Nakaya et al. (Proceedings of Symposium on Perfluorochemical Artificial Blood, Kyoto 1976, 187–201). They examined the viability of kidney in a biological way by perfusing a rabbit kidney with FC-43 emulsion (a perfluorotributylamine emulsion) for 9 hours at room temperature. As compared with a control group perfused with Ringer's solution, the kidney perfused with the FC-43 emulsion well retained the mitochondrion function and higher activity levels of glycolytic and gluconeogenetic key enzymes, indicating that the oxygen transportation by FC-43 exerts an effective influence on the retention of functions by the perfused kidney. The above-noted authors, however, directed their research efforts mainly to the biological aspect, but not to the transplantation of a preserved kidney. It is Bercowitz who reported the results of transplantation of a canine kidney preserved by perfusion containing a PFC emulsion [J. Surg. Res., 20, 595–600 (1976)]. He perfused a canine kidney for 24 hours at a low temperature with a PFC emulsion containing albumin and a cryoprecipitated plasma. The preserved kidney was then autotransplanted and the graft survival rate was examined. The rate was found to be 100% in all five cases, whereas the rate was 62% in five control cases out of eight where the perfusate contained no FC-43 emulsion, indicating significantly the advantage of the FC-43 system.

The two reports, cited above, showed that the PFC emulsion is an effective perfusate for preserving a kidney at both low temperatures and room temperature. However, the preservation periods described in both reports are not sufficiently long to ascertain the practicability of the preserving methods. Particularly, the FC-43 emulsion containing albumin is not sufficiently stable to produce a normalized preparation.

Under the aforementioned circumstances, the present inventors conducted studies on the PFC-43 containing perfusate for the long-period preservation of an organ, particularly kidney, for transplantation. Based on the results of such studies, the present invention has been accomplished.

The object of this invention is to provide a PFC perfusate and a method for the effective long-period preservation of organs for transplantation.

According to this invention, there are provided a perfusate for preserving an organ for transplantation, comprising a modified Ringer's solution characterized by containing potassium ion in a concentration of 8 to 20 meq/liter, albumin dissolved therein, and an emulsified liquid saturated perfluorocarbon compound and a method for the perfusional preservation of an organ for transplantation by the use of said perfusate.

The basal Ringer's solution used in the modified Ringer's solution of this invention is subject to no special restriction but can be a customary one or that modified by Locke, Tyrode, Earle, Hanks or Krebs. The modification according to this invention consists in that the potassium ion concentration is increased from the ordinary level of 4 to 6 meq/liter to 8 to 20, preferably 8 to 15 meq/liter. Such an increased concentration was adopted in order to approximate more closely the potassium ion level in the extracellular fluid. By the choice of such a concentration of potassium ion, it becomes possible to bring about a leaping increase in the graft survival rate of an organ, particularly kidney, preserved for a long period by perfusion. The modified Ringer's solution of this invention has an osmolarity of 290 to 300 m Osm/liter and a pH of 7.1 to 7.7 at 20° C. In Table 1 are shown, for reference, salt compositions of some typical Ringer's solutions modified according to this invention, together with that of a normal plasma which is a prototype of an ordinary Ringer's solution.

Talbe 1
Examples of electrolyte composition of modified Ringer's solution.
Units: meq/liter

| Ion | Modified Ringer's solution according to this inventon | | | Normal plasma |
|---|---|---|---|---|
| | No 1 | 2 | 3 | |
| $Na^+$ | 112 | 142 | 116 | 142 |
| $K^+$ | 11 | 8 | 10 | 5 |
| $Mg^{++}$ | 7 | 2 | 6 | 2 |
| $Ca^{++}$ | | 5 | | |
| $Cl^-$ | 118 | 103 | 15 | 103 |
| $HCO_3^-$ | 3 | 27 | 10 | 27 |
| $HPO_4^-$ | 2 | 2 | 101 | 2 |
| $SO_4^{--}$ | 7 | | 6 | |
| Glucose | 33 | | 139 | |
| Lactose | | 5 | | 5 |

The perfusion fluid for preserving an organ according to this invention is prepared by mixing together an emulsion of PFC in the modified Ringer's solution, albumin and the modified Ringer's solution so that the concentrations of PFC and albumin may assume respectively the predetermined values.

The PFC emulsion used in the invention is prepared from a liquid perfluorocarbon compound capable of absorbing oxygen by a known method disclosed in, for example, U.S. Pat. Nos. 3,958,014, 3,911,138, 3,962,439, or West German Patent Application DT-OS No. 2630586. These patent specifications discloses that a stable emulsion suitable for use as an artificial blood can be prepared by emulsifying a perfluorocarbon compound with a phospholipid as emulsifier (U.S. Pat. No. 3,958,014), a phospholipid and a $C_{8-22}$ fatty acid as auxiliary agent (U.S. Pat. No. 3,962,439); or by using a polyoxyethylene-polyoxypropylene copolymer (molecular weight 2,000 to 20,000) as nonionic emulsifier (U.S. Pat. No. 3,911,138); or by using a polyoxyethylene alkyl ether or polyoxyalkyl allyl ether or cojointly using the above-noted fatty acids, nonionic emulsifiers and the above-noted auxiliary emulsifying agent (West German Patent Application DT-OS No. 2630589).

The perfluorocarbon compounds to be emulsified are those not giving such adverse effects to the organs or tissues, and are saturated perfluorocarbon compounds preferably having as a whole 9 to 12 carbon atoms some or whole of which form at least one saturated alicyclic ring, heterocyclic ring together with hetero nitrogen atom and/or oxygen atom, aliphatic tertiary amine together with nitrogen atom or aliphatic ether together with oxygen atom or atoms.

The first group of the perfluorocarbon compounds used in the invention is a perfluoroalkane, perfluorocycloalkane or perfluoro(alkylcycloalkane) which includes, for example, perfluoro($C_{9-12}$-alkanes) such as perfluorodecane, and perfluorododecane; perfluoro($C_{3-5}$-alkylcyclohexanes) such as perfluoro(methylpropylcyclohexanes), perfluoro(butylcyclohexanes), perfluoro(trimethylcyclohexanes), perfluoro(ethylpropylcyclohexanes) and perfluoro(pentylcyclohexanes); perfluorodecalin, perfluoro(methyldecalins) and perfluoro(dimethyldecalins).

The second group is a perfluoro(alkylsaturated heterocyclic compound) which includes, for example, perfluoro(alkyltetrahydropyrans) such as perfluoro(butyltetrahydropyrans), perfluoro(pentyltetrahydropyrans) and perfluoro(hexyltetrahydropyrans); perfluoroalkyltetrahydrofurans) such as perfluoro(pentyltetrahydrofurans), perfluoro(hexyltetrahydrofurans) and perfluoro(heptyltetrahydrofurans); perfluoro(N-alkylpiperidines) such as perfluoro(N-pentylpiperidines), perfluoro(N-hexylpiperidines) and perfluoro(N-butylpiperidine); and perfluoro(N-alkylmorpholines) such as perfluoro(N-pentylmorpholines), perfluoro(N-hexylmorpholines) and perfluoro(N-heptylmorpholines).

The third group is a perfluoro(tert-amine) which includes, for example, perfluoro(tributylamine), perfluoro(diethylhexylamine), perfluoro(dipropylbutylamine) and perfluoro(diethylcyclohexylamine); and a perfluoro(dioxaalkane), that is, perfluoro(alkylene glycol dialkyl ether), such as perfluoro(3,8-dioxa-2,9-dimethyldecane) or perfluoro(tetramethylene glycol diisopropyl ether), perfluoro(3,7-dioxa-2,8-dimethylnonane) or perfluoro(trimethylene glycol diisopropyl ether) and perfluoro(4,6-dioxa-5,5-dimethylnonane), or perfluoro(isopropylene glycol di-n-propyl ether).

The thus prepared emulsion of PFC in the modified Ringer's solution has a particle size of 0.05 to 0.3$\mu$, contains 10 to 50% (W/V) of PFC, 2.0 to 5% (W/V) of an emulsifier and, if necessary 0.1 to 1.0% (W/V) of an auxiliary emulsifier, and can be stored in stable state for a long period.

The present perfusate for preserving an organ for transplantation is prepared, before using, by mixing together the above PFC emulsion, a commercial bovine or human albumine and the aforementioned modified Ringer's solution so that the resulting fluid may contain 7.5 to 12.5% (W/V) of PFC, 1 to 8% (W/V) of albumin. If necessary, pharmaceuticals such as procaine hydrochloride, heparin, phenoxybenzamine, insulin, dexamethasone ("Decadron"), methylprednisolone, antibiotics and urokinase can be added. The limits of PFC concentration given above were set up in order to ensure the graft survival after transplantation of the organ preserved by perfusion of the fluid. The concentration of albumine within the above-mentioned limits is suitable for adjusting the colloid osmotic pressure so that the perfusion fluid may be kept physiologically isotonic.

The preservation of an organ to be transplanted is carried out in a customary way under oxygenation with oxygen by means of a customary equipment. For instance, 400 ml of a 25% (W/V) PFC emulsion, 360 ml of the modified Ringer's solution and 240 ml of a 25% (W/V) human albumine solution in the modified Ringer's solution are mixed together to make a total of 1 liter. The resulting mixture is fed to a perfusate reservoir and perfused through the organ for transplantation, while being oxygenated with a mixed gas (95–98% oxygen and 5–2% carbon dioxide) or oxygen alone by means of an oxygenator of the membrane type or bubbling type. The rate of circulation of the perfusate is 15 to 50 ml/g kidney/hour and the perfusate was oxygenated with 95% $O_2$–5% $CO_2$ at flow rate of 30 to 1500 ml/min. If necessary, the above-noted pharmaceuticals can be added to the perfusate, without causing deterioration of the perfusate. In the perfusional preservation, it is also possible to recycle, by means of a pulsatile pump, the perfusate fed to the artery side reservoir of an organ preservation equipment. In the long-period preservation, it is desirable to refresh appropriately the perfusate. The perfusate of this invention can be used not only in perfusional preservation but also in the field of bench surgery.

The method of this invention makes it possible to preserve an organ very safely for a long period until the time of transplantation. Since the graft survival rate is very high, the present method will assure commercial success of organ transplantation in the field of practical medical treatment.

Illustrative examples of the methods of preparing each component of the present perfusate and the procedure of preparing the perfusate are described below. The symbol "% (W/V)" referred to in the specification and claims of this application means the amount proportion of a material by weight (grams) based on 100 ml of the resulting liquid.

PREPARATION EXAMPLE 1

Preparation of fluorocarbon emulsion:

In 8 liters of a modified Ringer's solution (described later), was dissolved 300 g of a polyoxyethylene-polyoxypropylene copolymer (molecular weight 8,350). After addition of 3 kg of perfluorodecalin, the resulting mixture was stirred in a mixer to form a coarse emulsion. The coarse emulsion was fed to the reservoir of a jet-type emulsifier (Monton-Gaulin type homogenizer) to circulate the emulsion. Emulsification was carried out at 35°±5° C. under a pressure of 200 to 500 kg/cm². The concentration of perfluorodecalin in the resulting fine emulsion was 31.3% (W/V) and the average particle diameter was 0.09 to 0.1$\mu$, as measured by the method of centrifugal sedimentation. After 6 months of storage of the emulsion at 4° C., coalescence of the particles was not noticed and the average particle diameter remained substantially unchanged.

Preparation of albumin solution:

A commercial preparation of human serum albumin was dissolved in a concentration of 25% (W/V) in the modified Ringer's solution described below.

Preparation of modified Ringer's solution:

A modified Ringer's solution was prepared by dissolving in distilled water, in terms of g/liter, 6.51 NaCl, 0.4 $MgSO_4$, 0.8 KCl, 0.24 $NaHCO_3$, 0.14 $Na_2HPO_4$, 6.0 glucose, forming a solution of the following electrolyte composition, in terms of meq/liter: 112 $Na^+$, 11 $K^+$, 7 $Mg^{++}$, 118 $Cl^-$, 3 $HCO_3^-$, 2 $HPO_4^{--}$, 7 $SO_4^{--}$, 33 glucose.

Mixing of component fluids:

A 570 ml portion of the modified Ringer's solution and 330 ml of the fluorocarbon emulsion were mixed and thoroughly stirred. The mixture was sterilized by heating in a sterilizer at 115° C. for 12 minutes. The sterilized mixture was mixed with 100 ml of the albumin solution which had been passed through a bacterial filter. The resulting mixture was stored in cool place at 1° to 10° C. and used at need as a perfusion fluid for preserving an organ for transplantation.

PREPARATION EXAMPLE 2

Preparation of perfluorocarbon emulsion:

In 8 liters of the modified Ringer's solution, was dissolved 330 g of polyoxyethylene octyl ether having an average molecular weight of 3,500. To the solution, were added 40 g of soybean phospholipid and 2 g of potassium oleate. The mixture was stirred in a mixer to form a suspension. The suspension was admixed with 3 kg of perfluoro (tributylamine) and stirred in a mixer to form a coarse emulsion. The coarse emulsion was further emulsified in the same manner as in Example 1. The fine emulsion thus obtained was divided into vails and sterilized by heating in a rotary sterilizer at 115° C. for 12 minutes. The concentration of the perfluorocarbon in the sterized emulsion was 29.7% (W/V). On storage at 4° C. for 6 months, the emulsion showed no coalescence of the particles.

Mixing of component fluids:

A 550 ml portion of the modified Ringer's solution used in Preparation Example 1, 100 ml of the albumin solution and 350 ml of the fluorocarbon emulsion obtained above were mixed. The mixed fluid was stored in cool place at 1° to 10° C. and used, when needed, as a perfusion fluid for preserving an organ to be transplanted.

PREPARATION EXAMPLE 3

The procedures in Preparation Example 1 were repeated, except that perfluoromethylpropylcyclohexane was used in place of the perfluorodecalin. The perfusion fluid obtained was similar in properties to that obtained in Preparation Example 1.

PREPARATION EXAMPLE 4

The procedures in Preparation Example 1 were repeated, except that each of the perfluorobutylcyclohexane, perfluorotrimethylcyclohexane, perfluoroethylpropylcyclohexane, perfluoromethyldecalin, perfluorohexyl tetrahydropyran, perfluoropentyltetrahydrofuran, perfluoroheptyltetrahydrofuran and perfluorodecane was used in place of the perfluorodecalin. The perfusion fluids obtained were similar to that obtained in Preparation Example 1.

PREPARATION EXAMPLE 5

The procedures in Preparation Example 1 were repeated, except that each of the perfluoro N,N-dibutylmonomethylamine, perfluoro N,N-diethylpentylamine, perfluoro N,N-dipropylbutylamine, perfluorotripropylamine, perfluoro N,N-diethylcyclohexylamine, perfluoro N-pentylpiperidine, perfluoro N-hexylpiperidine, perfluoro N-butylpiperidine, perfluoro N-pentylmorpholine, perfluoro N-hexylmorpholine, and perfluoro N-heptylmorpholine was used in place of the perfluorodecalin. The perfusion fluids obtained were similar to that obtained in Preparation Example 1.

PREPARATION EXAMPLE 6

The procedures of Preparation Example 1 were repeated, except that perfluorotributylamine was used in place of the perfluorodecalin. The perfusion fluid obtained was similar to that obtained in Preparation Example 1.

PREPARATION EXAMPLE 7

The procedure of Preparation Example 1 was repeated, except that a polyoxyethylene-polyoxypropylene copolymer having a molecular weight of 15,800 was used in place of the copolymer having a molecular weight of 8,350. The perfusion fluid obtained was similar in properties to that obtained in Preparation Example 1.

Below are shown examples of comparative experiments to demonstrate by animal experiments the effectiveness of the perfusional preserving fluids of this invention in transplantation of the kidney preserved by perfusion. The survival or death of the graft was determined by observing the function of the grafted kidney after the contralateral normal kidney had been removed. In the tables, the term "early function" means that urination was observed in two days after the contralateral nephrectomy; the term "late function" means that no urination was observed in two days after the contralateral nephrectomy but afterwards the function of the kidney gradually improved until urination was observed and the animal under test had survived; the term "necrosis" means the death of the tissues in localized areas of the transplanted kidney before the contralateral nephrectomy (the experiment was discontinued); and "A.T.N." (acute tubular necrosis) means that after the contralateral nephrectomy the animal suffered from anuria, loss of appetite and frequent vomiting until death due to acute renal insufficiency.

EXPERIMENT EXAMPLE 1

Optimal PFC concentration in preserving fluid:

It is necessary and essential to determine the PFC concentration most suitable for perfusion, because with the increase in PFC concentration of an PFC emulsion, the oxygen carrying capacity of the emulsion increases, while, on the other hand, the viscosity increases considerably at low temperatures. In order to determine the optimal PFC concentration during perfusion, a series of perfusion fluids with varied PFC concentrations were prepared using as the basal saline solution a modified Collin's solution (M.S.C.) [The Lancet, 2, 1219–1222 (1969)], which is said to be the most favorable for hypothermic storage of organs and has an electrolyte composition resemble to intracellular fluid. Varid amounts of the fluorocarbon emulsion obtained in Preparation Example 2 were added to M.C.S. so that the ultimate PFC concentrations in the perfusion fluids thus obtained may become 5, 7.5, 10, 12.5 and 15% (W/V). Experiments were run to preserve canine kidneys for transplantation by perfusion with the above fluids at 5° to 8° C. at the perfusion flow rate of 15 to 18 ml/g/hour for 24 hours under oxygenation with an oxygen-containing gas (95%$O_2$, 5% $CO_2$) at a flow rate of 300 to 500 ml/minute. By using five dogs per group, the preserved kidneys were autotransplanted. On the 7th day after autotransplantation, the contralateral normal kidney of each dog was excised and the subsequent survival days of each dog were counted. When a dog survived for 4 weeks or longer, the graft survival was assumed to be positive, because in such a dog, after 2 weeks both BUN (blood urea nitrogen) and creatinine levels remained normal and urination was observed. From the data obtained, the optimal PFC concentration in the perfusate was determined.

The experiment was run in a customary way in accordance with the following procedural sequence:

| | |
|---|---|
| Anesthesia: | Pentobarbital sodium (30 mg/kg i.v. |
| 75 | injection) Endotracheal administration |
| 75 | of halothane and oxygen |
| Midline abdominal incision | |
| 75 | |
| Surgical isolation of left kidney | |
| 75 | |
| Cannulation (ureter, renal artery and vein) | |
| 75 | |
| Initial wash out with cold M.C.S. or cold Ringer's lactate solution | |
| 75 | |
| Connect to the perfusion circuit | |
| 75 | Perfusional preservation with oxygenated |
| 75 | perfusate at 5° to 8° C. for 24 hours |
| 75 | or 72 hours |
| Wash out (M.C.S. or Ringer's lactate solution) | |
| 75 | |
| Autotransplantation into femoral fossa | |
| 75 | |
| Delayed contralateral nephrectomy | |

Table 2

Effect of PFC Concentration Perfusate on Graft Survival

| Dog No. | Perfusates | Survival time (days) | Survival | Remarks |
|---|---|---|---|---|
| 1 | | *Alive | | Early function |
| 2 | | — | | necrosis |
| 3 | M.C.S. | 5 | 2/5 | **A.T.N. (Anuria) |
| 4 | | Alive | | Early function |
| 5 | | 4 | | A.T.N.(Anuria) |
| 6 | | — | | Necrosis |
| 7 | | Alive | | Late function |
| 8 | 5% PFC in M.C.S. | 5 | 3/5 | A.T.N.(Anuria) |
| 9 | | Alive | | Early functon |
| 10 | | Alive | | Late function |
| 11 | | Alive | | Early function |
| 12 | | Alive | | Early function |
| 13 | 7.5% PFC in M.C.S. | Alive | 4/5 | Early function |
| 14 | | 7 | | A.T.N.(Anuria) |
| 15 | | Alive | | Early function |
| 16 | | Alive | | Early function |
| 17 | | 5 | | A.T.N.(Anuria) |
| 18 | 10% PFC in M.C.S. | Alive | 4/5 | Early function |
| 19 | | Alive | | Early function |
| 20 | | Alive | | Early function |
| 21 | | Alive | | Early function |
| 22 | | Alive | | Early function |
| 23 | 12.5% PFC in M.C.S. | Alive | 4/5 | Early function |
| 24 | | 5 | | A.T.N.(Anuria) |
| 25 | | Alive | | Early function |
| 26 | | 8 | | A.T.N. (Hematuria) |
| 27 | | Alive | | Early function (Hema.) |
| 28 | 15% PFC in M.C.S. | 4 | | A.T.N.(Anuria) |
| 29 | | Alive | 2/5 | Early function (Hema.) |
| 30 | | 7 | | A.T.N.(Anuria) |

*Alive: Survived for longer than 4 weeks.
**A.T.N. (Acute tubular necrosis)

The results obtained were as shown in Table 2. As is seen from Table 2, a high rate of graft survival was obtained at a PFC concentration of 7.5 to 12.5% (W/V). If the PFC concentration exceeds 12.5% (W/V) and reaches 15% (W/V), hematuria was observed in all cases on resumption of the blood flow after transplantation. Two dogs who survived for over 2 weeks showed the sign of hematuria for several days after contralateral nephrectomy, then recovered and survived. From the above results it was concluded that a perfusion fluid adjusted to a PFC concentration of 10% (W/V) is most effective for the perfusional preservation of an excised kidney.

EXPERIMENT EXAMPLE 2

Basal salt solution:

Long-period low temperature perfusional preservation experiments were carried out in order to select a suitable basal salt solution. The salt solutions examined were M.C.S. (described before), Ringer's solution and modified Ringer's solution (M.R.S.) prepared in Preparation Example 1. Perfusion fluids for preservation were prepared by adding the perfluorocarbon emulsion of Preparatoin Example 2 and the bovine serum albumin to a salt solution so that the ultimate concentration may become 10% (W/V) of PFC and 6% (W/V) of albumin. Perfusion was carried out on canine kidneys (5 per group) at 5° to 8° C. for 72 hours following the procedure of Experiment Example 1. After transplantation and resumption of the blood flow, examinations were made on the movement of blood through the kidney, color and tone of the kidney, irination, and symptoms due to contralateral nephrectomy performed on the 7th day after transplantation. The perfusate (2,000 ml in total volume) was not refreshed during 72 hours of perfusion but recycled at a rate of 15–18 ml/g/hour. Except for the cases where M.R.S. was used as the basal salt solution, the results of transplantation were very unfavorable and almost all of the test animals died due to acute kidney insufficiency in 10 days after the contralateral nephrectomy. On the contrary, in the cases where M.R.S. was used as the basal salt solution, all of the animals recovered uneventfully without exception.

EXPERIMENT EXAMPLE 3

Effect of albumin concentration in perfusate on canine kidney:

The persusates used in this experiment were 10% PFC emulsion in modified Ringer's solution, which was prepared by the use of PFC emulsion prepared in Preparation Example 6, and contained different concentrations of human albumin. The kidneys were perfused for 72 hours at 5° to 8° C. under oxygenation with the oxygen-containing gas used in Experimental Example 1 at a flow rate of 300 to 500 ml/min and then autotransplanted as in Experiment Example 1. The perfusion flow rate was maintained between 15 and 18 ml/g/hour during perfusion. The contralateral nephrectomy was carried out one week later after autotransplantation.

The results were as shown in Table 3.

Table 3

| Dog No. | Concentration of albumin (%) | Kidney weight gain during perfusion (%) | After contralateral nephrectomy | |
|---|---|---|---|---|
| | | | Function | Survival |
| 1 | 0 | 73.5 | No function | Died |
| 2 | | 49.4 | No function | Died |
| 3 | | 53.1 | Late function 2 days | Survived |
| 4 | | 38.4 | Late function 2 days | Survived |
| 5 | 2 | 52.9 | No function | Died |
| 6 | | 49.8 | No function | Died |
| 7 | | 37.6 | No function | Died |
| 8 | 4 | 20.3 | Early function | Survived |
| 9 | | 41.6 | Early function | Survived |
| 10 | | 13.7 | Early function | Survived |
| 11 | 6 | 30.6 | Early function | Survived |
| 12 | | 34.4 | Early function | Survived |
| 13 | | 11.9 | Early function | Survived |
| 14 | 8 | 22.8 | Early function | Survived |
| 15 | | 30.5 | No function | Died |

EXPERIMENT EXAMPLE 4

Long-period low temperature perfusion of kidney for transplantation:

Transplantation experiments on canine kidneys out in a manner similar to that in Experiment Example 1. Each kidney was preserved for one week by perfusion at 5° to 8° C. and a perfusion flow rate of 15 to 18 mg/g/hour under oxygenation with the gas at a flow rate of 300 to 500 ml/min. The perfusion fluid was prepared by using the M.R.S. of Preparation Example 1 as the basal salt solution and adding thereto bovine serum albumin and the PFC emulsion of Preparation Example 2 or a PFC emulsion prepared in the same manner as in Preparation Example 2, except that perfluorodecalin was used in place of the perfluorotributylamine. The concentrations of albumin and PFC in the perfusion fluid were 6% (W/V) and 10% (W/V), respectively. After one week of the perfusional perservation, the kidneys were autotransplanted as in Experiment Example 1. The contralateral nephrectomy was carried out after one week from the autotransplantation and symtoms were observed. The results were as shown in Table 4. The plasma levels of creatinine and BUN of the survived animals became normal in 3 weeks.

Table 4

| Example No. | Perfusate | Kidney weight gain during perfusion (%) | After contralateral nephrectomy | |
|---|---|---|---|---|
| | | | Function | Survival |
| 1 | | 34.3 | Early function | Survival |
| 2 | M.R.S. albumin | 46.9 | No function | died |
| 3 | 6% (W/V) Perfluorotributylamine | 20.1 | Late function 2 days | Survival |
| 4 | | 18.7 | Late function 3 days | Died |
| 5 | 10% (W/V) M.R.S. albumin 6% (W/V) Perfluorodecalin 10% (W/V) | 33.5 | Early function | Survival |
| 6 | | 19.3 | Early function | Survival |
| 7 | | 40.1 | Late function 3 days | Died |
| 8 | | 40.9 | Early function | Survived |
| 9 | | 23.5 | Early function | Survived |
| 10 | | 21.6 | No function | Died |

EXPERIMENT EXAMPLE 5

Using canine kidneys, transplantation experiments were conducted similarly to Experiment Example 1. Each kidney was preserved at 18° to 22° C. for 12 or 24 hours by perfusion at a perfusion flow rate of 40 to 50 ml/g/hour under oxygenation with the mixed gas (95%$O_2$–5%$CO_2$) at a flow rate of 300 to 500 ml/min. The perfusion fluid was prepared by using the M.R.S. of Preparation Example 1 as the basal salt solution and adding thereto the PFC emulsion of Preparation Example 2 and a bovine serum albumin. The concentrations of the PFC and albumin in the perfusion fluid were 10%(W/V) and 6%(W/V), respectively. After 12 hours or 24 hours of preservation, the kidneys were autotransplanted. The contralateral nephrectomy was carried out one week after the autotransplantation and the symptomes were observed. In Table 5 are shown the results of the above experiments, together with the results of a control experiment wherein no PFC was added and a comparative experiment wherein M.C.S. was used as the basal salt solution.

Table 5

| Example No. | Perfusate | Hours of perfusion | After contralateral nephrectomy | |
|---|---|---|---|---|
| | | | Function | Survival |
| 1 | M.R.S. | 12 | No function | Died |
| 2 | albumin 6% | | " | " |
| 3 | (W/V) | | " | " |
| 4 | | | " | " |
| 5 | M.C.S. | 12 | No function | Died |
| 6 | albumin 6% | | " | " |
| 7 | (W/V) | | " | " |
| 8 | PFC 10% (W/V) | | " | " |
| 9 | M.R.S. | 12 | Early function | Survived |
| 10 | albumin | | " | " |
| 11 | 6%(W/V) | | " | " |
| 12 | PFC 10% (W/V) | | " | " |
| 13 | M.R.S. | 24 | Early function | Survived |
| 14 | albumin | | No function | Died |
| 15 | 6%(W/V) | | Early function | Survived |
| 16 | PFC 10% (W/V) | | Late function | Survived |

Table 5-continued

| Example No. | Perfusate | Hours of perfusion | After contralateral nephrectomy | |
|---|---|---|---|---|
| | | | Function | Survival |
| | | | 2 days | |

What is claimed is:

1. A liquid for the perfusional preservation of an organ for transplantation, comprising a modified Ringer's solution characterized by containing potassium ion in a concentration of 8 to 20 meq/liter, and effective amounts of albumin dissolved therein, a liquid perfluorocarbon compound emulsified therein, and an emulsifier.

2. The liquid of claim 1 which contains the albumin in concentrations of 1 to 8%(W/V).

3. The liquid of claim 1 which contains the perfluorocarbon compound in a concentration of 7.5 to 12.5%(W/V).

4. The liquid of claim 1, wherein the perfluorocarbon compound has 9 to 12 carbon atoms.

5. The liquid of claim 4, wherein the perfluorocarbon compound is at least one member selected from the group consisting of perfluoroalkylcyclohexane having 3 to 5 carbon atoms in the alkyl, perfluorodecalin, perfluoro methyldecalin, perfluoroalkyltetrahydropyran having 4 to 6 carbon atoms in the alkyl, perfluoro alkyltetrahydrofuran having 5 to 7 carbon atoms in the alkyl, perfluoro alkylpiperidine having 4 to 6 carbon atoms in the alkyl, perfluoro alkylmorpholine having 5 to 7 carbon atoms in the alkyl, perfluoro trialkylamine, perfluoro(diethylcyclohexylamine), and perfluoro(dioxaalkane).

6. The liquid of claim 4, wherein the perfluorocarbon compound is perfluoro alkylcyclohexane having 3 to 5 carbon atoms in the alkyl, perfluorodecalin or perfluoro methyldecalin.

7. The liquid of claim 4, wherein the perfluorocarbon compound is perfluoro alkyltetrahydropyran having 4 to 6 carbon atoms in the alkyl, perfluoro alkyltetrahydrofuran having 5 to 7 carbon atoms in the alkyl, perfluoro alkylpiperidine having 4 to 6 carbon atoms in the alkyl, or perfluoro alkylmorpholine having 5 to 7 carbon atoms in the alkyl.

8. The liquid of claim 4, wherein the perfluorocycloalkane is perfluorodecalin, perfluoro(methyldecalin) or perfluoro(dimethyldecalin).

9. The liquid of claim 6, wherein the perfluorocycloalkane is perfluoro(butylcyclohexane), perfluoro(methylpropylcyclohexane), perfluoro(trimethylcyclohexane), perfluoro(ethylpropylcyclohexane) or perfluoro(pentylcyclohexane).

10. The liquid of claim 7, wherein the perfluoro-saturated-heterocyclic compound is perfluoro(butyltetrahydropyran), perfluoro(pentyltetrahydrofuran), perfluoro(hexyltetrahydrofuran), perfluoro(heptyltetrahydrofuran), perfluoro(N-hexylpiperidine), perfluoro(N-pentylmorpholine), perfluoro(N-hexylmorpholine) or perfluoro(N-heptylmorpholine).

11. The liquid of claim 4, wherein the perfluorocarbon compound is a perfluoro trialkylamine, perfluoro(diethylcyclohexylamine) or perfluoro(dioxaalkane).

12. The liquid of claim 11, wherein the perfluorocarbon compound is a perfluoro-tert-amine which is perfluoro(diethylhexylamine), perfluoro(dipropylbutylamine), perfluoro(diethylcyclohexylamine) or perfluoro(tributylamine).

13. The liquid of claim 11, wherein the perfluorocarbon compound is a perfluoro(dioxaalkane) which is perfluoro(tetramethylene glycol diisopropyl ether), perfluoro(trimethylene glycol diisobutyl ether) or perfluoro(isopropylidene glycol di-n-propyl ether).

14. The liquid of claim 1, wherein the emulsifier is a polyoxyethylene-polyoxypropylene copolymer, polyoxyethylene alkyl ether, polyoxyalkyl allyl ether or a phospholipid or a mixture thereof.

15. The liquid of claim 1, wherein a $C_{8-21}$-fatty acid is present together with the emulsifier, said fatty acid being an auxiliary emulsifier.

16. A process for preserving an organ to be transplanted comprising perfusing the organ with a perfusion liquid containing a perfluorocarbon compound under oxygenation, characterized in that the perfusion liquid is a mixture of effective amounts of albumin, a Ringer's solution which has been modified in the amount of potassium ion by increasing the amount to 8–20meq/liter, and a stable emulsion of a perfluorocarbon emulsion, the concentration of albumin being 1–8%(W/V) and that of the perfluorocarbon compound being 7.5 to 12.5%(W/V) based on the perfusion liquid.

* * * * *